United States Patent
Nöcker et al.

(10) Patent No.: US 11,103,429 B2
(45) Date of Patent: Aug. 31, 2021

(54) PROCESS FOR TREATING HAIR

(71) Applicant: KAO GERMANY GMBH, Darmstadt (DE)

(72) Inventors: Bernd Nöcker, Darmstadt (DE); Steven Breakspear, Darmstadt (DE); Peter Bauer, Darmstadt (DE); Manfred Dürr, Darmstadt (DE)

(73) Assignee: KAO GERMANY GMBH, Darmstadt (DE)

( * ) Notice: Subject to any disclaimer, the term of this patent is extended or adjusted under 35 U.S.C. 154(b) by 309 days.

(21) Appl. No.: 15/757,849

(22) PCT Filed: Mar. 15, 2016

(86) PCT No.: PCT/EP2016/055589
§ 371 (c)(1),
(2) Date: Mar. 6, 2018

(87) PCT Pub. No.: WO2017/041909
PCT Pub. Date: Mar. 16, 2017

(65) Prior Publication Data
US 2018/0338894 A1 Nov. 29, 2018

(30) Foreign Application Priority Data

Sep. 8, 2015 (EP) .................................... 15184305

(51) Int. Cl.

| | |
|---|---|
| *A61K 8/22* | (2006.01) |
| *A61K 8/362* | (2006.01) |
| *A61K 8/365* | (2006.01) |
| *A61K 8/44* | (2006.01) |
| *A45D 7/04* | (2006.01) |
| *A61K 8/19* | (2006.01) |
| *A61Q 5/04* | (2006.01) |
| *A61Q 5/10* | (2006.01) |
| *A45D 7/00* | (2006.01) |

(52) U.S. Cl.
CPC .................. *A61K 8/22* (2013.01); *A45D 7/04* (2013.01); *A61K 8/19* (2013.01); *A61K 8/362* (2013.01); *A61K 8/365* (2013.01); *A61K 8/44* (2013.01); *A61Q 5/04* (2013.01); *A61Q 5/10* (2013.01); *A45D 2007/001* (2013.01); *A61K 2800/4324* (2013.01); *A61K 2800/805* (2013.01); *A61K 2800/882* (2013.01); *A61K 2800/884* (2013.01)

(58) Field of Classification Search
None
See application file for complete search history.

(56) References Cited

U.S. PATENT DOCUMENTS

| 2004/0086475 A1 | 5/2004 | Boswell et al. |
| 2015/0034119 A1 | 2/2015 | Pressly et al. |
| 2015/0037270 A1 | 2/2015 | Pressly et al. |

FOREIGN PATENT DOCUMENTS

| EP | 1 655 056 A1 | 5/2006 |
| EP | 2 020 254 A1 | 2/2009 |
| EP | 2 020 255 A1 | 2/2009 |
| EP | 2 191 864 A1 | 6/2010 |
| EP | 2 191 865 A1 | 6/2010 |
| JP | 2000128747 A | * 5/2000 |
| WO | 2015/017768 A1 | 2/2015 |

OTHER PUBLICATIONS

English Translation of JP 2000128747 A (Year: 2000).*
International Search Report dated May 2, 2016, dated May 13, 2016.

* cited by examiner

*Primary Examiner* — Nicole P Babson
(74) *Attorney, Agent, or Firm* — Norris McLaughlin, P.A.

(57) ABSTRACT

The present invention relates to a process for permanent shaping and dyeing carried out one after another with compositions providing improved and milder shaping and dyeing of hair, especially human hair. The inventors of the present invention have unexpectedly found out that when commonly used permanent shaping and dyeing compositions are mixed with another composition comprising predominantly carboxylic acids, the permanent shaping and dyeing effects of the compositions are improved, homogeneous permanent shaping and dyeing of hair fibers is achieved and natural cosmetic properties of hair are maintained.

20 Claims, No Drawings

PROCESS FOR TREATING HAIR

This application is the U.S. National Stage of International Application No. PCT/EP2016/055589, filed Mar. 15, 2016, which claims foreign priority benefit under 35 U.S.C. § 119 of European Application No. EP15184305.9 filed Sep. 8, 2015 the disclosures of which are incorporated herein by reference.

The present invention relates to a permanent shaping and dyeing process carried out one after another with compositions providing improved and milder shaping and dyeing of hair, especially human hair.

Hair dyeing and permanent shaping are carried out usually as two separate processes. Hair dyeing, especially under oxidative conditions, involves applying to hair a strongly oxidative composition comprising the dyestuff precursors and optionally coupling substances onto hair and leaving it for a certain period of time, usually at elevated temperatures, in order to allow for penetration of the relatively small uncolored dye precursors into the hair. In combination with the action of strong oxidizing agents, the dye precursors polymerize to larger molecules so that they may not be easily eluted from the hair. At the same time the effect of the oxidizing agent is to lighten the hair color to provide a relatively homogeneous dyeing base. Since the process involves the use of strong oxidative compositions, the hair fiber itself is negatively affected by such treatment and it consequently loses its certain natural cosmetic properties such as its strength against breaking, its natural elasticity, its natural shine and natural soft feel upon touching.

On the other hand, permanent shaping of hair involves application of a strongly reductive composition onto hair and leaving it for a certain period of time usually at elevated temperatures in order to open up the disulfide bonds and rebuilding them in the preferred shape with an application of a mild oxidative composition. Since the process involves the use of strong reductive and oxidative compositions, the hair fiber itself is affected by such treatment and therefore it also loses its certain natural properties such as its strength against breaking, its natural elasticity, its natural shine and natural soft feel upon touching.

Moreover, the to be dyed and/or permanently shaped hair is not always homogeneous in its physicochemical status as it may be damaged due to previous chemical treatments such as dyeing and permanently shaping and/or environmental effects. This often leads to inhomogeneous permanent shaping performance and/or inhomogeneous dyeing and, therefore, often consumers' dissatisfaction. There is, therefore, a great need for milder and more effective permanent shaping compositions which overcome one or more of the above mentioned problems.

There have been attempts to combine the two processes which have been successful to a certain extent. For example EP1655056, EP2020254, EP2020255, EP2191865 and EP2191864 disclose processes for permanent shaping and dyeing hair. However, these documents do not deal with the core of the present invention.

Recently in a series of patent applications (US2015/0034119, US2015/0037270, WO2015/017768) methods are published which claim benefits of the combined use of a bismaleate based binding agent in hair chemical treatments such as oxidative hair dyeing, permanently shaping and bleaching for improving hair structure. The publications are silent on the core of the present invention.

After a long research and careful considerations of the consumers' needs, the inventors of the present invention have unexpectedly found out that when commonly used permanent shaping compositions and dyeing compositions are mixed with another composition comprising predominantly carboxylic acids, the permanent shaping effect and dyeing effects are very much improved, homogeneous permanent shaping and dyeing of hair fibers is achieved and natural cosmetic properties of hair are maintained when the two processes are carried out one after another without the need of two separate hairdresser visits which saves time and certainly is more economical for the consumers.

Therefore the first object of the present invention is a process for treating hair, especially human hair, comprising the following steps:

a) hair is washed with a cleansing composition and towel dried,
b) hair is applied an aqueous composition (composition A) comprising one or more reducing agents, one or more alkalizing agents and has an alkaline pH in the range of 7.5 to 12.0, and is left on hair from 1 to 30 min,
c) hair is rinsed off with water
d) optionally hair is applied a composition C,
wherein the composition C is an aqueous composition comprising one or more oxidizing agents, preferably hydrogen peroxide, and has a pH in the range from 1.5 to 5,
e) Hair is applied an aqueous composition consisting of two compositions B and C,
wherein B is an aqueous composition comprising one or more hair dyes and one or more alkalizing agents and has an alkaline pH preferably in the range of 7.1 to 12,
wherein the mixed composition has an alkaline pH and is obtained by mixing the compositions B and C immediately before application onto hair and left on the hair for a period of 1 to 45 min,
f) Hair is rinsed off and optionally washed with a cleansing composition and dried,
wherein the composition(s) in step(s) b and/or e is (are) mixed with a composition D immediately before application onto hair for obtaining ready to use compositions,
wherein the composition D comprises
i) one or more carboxylic acids having three or more carboxyl groups and/or their salts, and
ii) one or more additional organic acid and/or their salts having one or two carboxyl groups,
wherein the composition D comprises the acids of i) and ii) and/or their salts at a total concentration of 10% to 100% by weight calculated to the total of composition D,
wherein the ready to use compositions in steps b and/or e have a pH in the range from 6.5 to 11 and comprise the acids and/or their salts at a total concentration in the range of 1% to 10% by weight calculated to the total of the ready to use compositions,
wherein the hair is optionally put under tension before or during or after application of reducing composition in step b and the tension is released from hair before application of the composition in step e.

The second object is a kit for hair, especially human hair, comprising the compositions A, B, C and D.

The composition A comprises one or more reducing agents. Useful are thioglycolic acid and/or its salts, cysteamine and/or its salts, thioglycerin and/or its salts, glycerin esters of thioglycolic acid and/or its salts, thiolactic acid and/or its salts, cysteine or its derivatives and/or its salts and sodium sulfite. Preferred are thioglycolic acid and/or its salts, thiolactic acid and/or its salts and cysteine or its derivatives and/or its salts. The most preferred is thioglycolic acid and/or its salts.

One or more reducing agents are comprised in the composition A at a concentration in the range of 1% to 15%, preferably 2% to 15%, more preferably 3% to 12.5% and most preferably 5% to 11% by weight calculated to the total of composition A.

The composition A comprises one or more alkalizing agents. Suitable ones are ammonia and alkyl- or alkanolamines according to the general structure

wherein $R_1$, $R_2$, and $R_3$ are same or different H, from $C_1$ to $C_4$, $C_3$ to $C_4$ unsaturated alkyl, $C_3$ to $C_4$ branched alkyl, $C_1$ to $C_4$ hydroxyl alkyl, $C_3$ to $C_4$ unsaturated hydroxyl alkyl, $C_3$ to $C_4$ branched hydroxyl alkyl, with the condition that at least one of $R_1$, $R_2$, or $R_3$ is different from H, wherein the alkalizing agents preferably selected from ammonia, monoethanolamine, and aminomethylpropanol, and particularly suitable one is aminomethylpropanol.

The alkalizing agent is comprised in the composition A at a total concentration of 1% to 20%, preferably 1% to 17.5%, more preferably 2% to 15% and most preferably 2.5% to 13% by weight calculated to the total of the composition A.

The composition A has a pH in the range of 7.5 to 12, preferably 8 to 11, and more preferably 8.5 to 10.5 and most preferably 8 to 10 measured at 20° C.

The composition B comprises one or more hair dyes. Suitably, the composition B comprises one or more oxidative dye precursors and optionally one or more coupling substances.

Suitable non-limiting examples of oxidative dye precursor classes are p-phenylendiamines, p-aminophenols, and heterocyclic compounds such as diaminopyrazols and substituted pyrimidines, and suitable coupling substances are resorcinols, m-aminophenols, m-phenylendiamines, pyridines and its derivatives, and naphthols.

Non-limiting examples of the oxidative dye precursor compounds are p-phenylenediamine, p-aminophenol, 2,5-diamino-toluene, 2-n-propyl or 2-ethyl-p-phenylenediamine, 2,6-di-methyl-p-phenylene-diamine, 2-(2,5-diaminophenyl) ethanol, 1-amino-4-bis-(2'-hydroxy-ethyl)aminobenzene, 2-(2-hydroxyethyl amino)-5-aminotoluene, 4,4'-diaminodiphenylamine, 4-aminodiphenylamine, 2-amino-5-N,N-diethyl aminotoluene, 4-amino-N-ethyl-N-isopropyl aniline, 2-chloro-p-phenylenediamine, 1-β-hydroxyethyl-2,5-diamino-4-chlorobenzene, 1-β-hydroxyethyl-2,5-diamino-4-methyl benzene, 2-methoxy-p-phenylenediamine, N,N-diethyl-p-phenylenediamine, 1-amino-4-β-methoxyethyl aminobenzene, 1-dimethyl-amino-4-aminobenzene, 1-hydroxy-2,5-diamino-4-methyl benzene, 1-hydroxymethyl-2,5-diaminobenzene, 1,3-dimethyl-2,5-diaminobenzene, 1,4-diamino isopropyl benzene and/or 1-amino-4-β-hydroxypropyl aminobenzene, 1-hydroxyethyl-4,5-diaminopyrazole, 3,4-diamino-5-hydroxypyrazole, 3,5-diaminopyrazole, 3,5-diamino pyrazol-1-carboxamide, 3-amino-5-hydroxypyrazole, 1-phenyl-2-methylpyrazole, 1-phenyl-3-methylpyrazole-5-one, 3,5-dimethylpyrazole, 3,5-dimethylpyrazole-1-methanol, 3,5-diamino-1,2,4-triazole, 4-aminophenol and the derivatives thereof such as 4-amino-3-methylphenol, 2-chloro-4-aminophenol, 2,6-dichloro-4-aminophenol, 2,4-diamino-phenol, 2,6-dibromo-4-aminophenol, tetraamino pyrimidines, triaminohydroxy pyrimidines, diaminomono- and -dihydroxy pyrimidines, aminotriazines, 5-amino salicylic acid and/or 1,2,4-triamino benzene, 2,5-diaminopyridine, 2,3-diaminopyridine, 2,6-diaminopyridine, 3-amino-2-methyl amino-6-methoxypyridine, 2-dimethyl-5-aminopyridine, 2-dimethyl aminoethyl-3-hydroxypyridine, 2-amino-4,6-dimethyl pyridine, 2-amino-3-hydroxypyridine, 3-amino-2(β-hydroxyethyl amino)-6-methoxy pyridine, 2,6-dimethyl amino-5-aminopyridine, 2-di(hydroxyethyl) amino-5-aminopyridine, 2-hydroxyethyl amino-5-aminopyridine, 4-hydroxy-2,5,6-triaminopyrimidine and/or the water-soluble salts thereof, and mixture thereof.

The total concentration of the dye precursors (developing substances) customarily ranges between 0.001% to 5%, preferably 0.01% to 4% and more preferably 0.05% to 3%, and most preferably 0.1% to 2% by weight, calculated to the total of the composition B.

The suitable non-limiting examples of the coupling substance if present in the composition B are 5-amino-2-methylphenol, 2-methyl-5-hydroxyethylaminophenol, 2,4,-diaminophenoxyethanol, 2-amino-4-hydroxyethylaminoanisol, 2-methyl-5-amino-6-chlorphenol, 1,3-bis(2,4-diaminophenoxy)propane, 2-bis(2-hydroxyethyl)aminotoluene, 2-amino-5-methylphenol, resorcinol, 2-methyl-resorcinol, 4-chlororesorcinol, 2-amino-4-chlorophenol, 5-amino-4-methoxy-2-methylphenol, 2-aminophenol, 3-aminophenol, 1-methyl-2-hydroxy-4-aminobenzene, 3-N,N-dimethyl aminophenol, 2,6-dihydroxy-3,5-dimethoxypyridine, 5-amino-3-methylphenol, 6-amino-3-methylphenol, 1,3-diamino-benzene, 1-amino-3-(2'-hydroxyethylamino)benzene, 1-amino-3-[bis(2'-hydroxyethyl) amino]benzene, α-naphthol, 4,6-dichlororesorcinol, 1,3-diamino-toluene, 4-hydroxy-1,2-methylenedioxy benzene, 1,5-dihydroxy naphthalene, 1,6-dihydroxy naphthalene, 1,7-dihydroxy naphthalene, 2,7-dihydroxy naphthalene, 1-hydroxy-2-methyl naphthalene, 4-hydroxy-1,2-methyldioxy benzene, 2,4-diamino-3-chlorophenol, 5-amino-2-methoxyphenol and/or 1-methoxy-2-amino-4-(2'-hydroxyethyl amino)benzene or the water-soluble salts thereof and mixture thereof.

In the composition B the coupling substance(s) as reaction partners of the developing substance(s) are present in approximately the same molecular proportions as the developing substances, i.e., at a total concentration in the range of 0.001% to 5%, preferably 0.01% to 4% and more preferably 0.05% to 3%, and most preferably 0.1% to 2% by weight, calculated to the total of the composition B.

Furthermore, the composition B comprises one or more hair direct dyes. Suitable ones are cationic, anionic and nitro dyes. Plant dyes are also suitable for the compositions of the present invention.

Suitable anionic direct dyes are Acid Black 1, Acid Blue 1, Acid Blue 3, Food Blue 5, Acid Blue 7, Acid Blue 9, Acid Blue 74, Acid Orange 3, Acid Orange 6, Acid Orange 7, Acid Orange 10, Acid Red 1, Acid Red 14, Acid Red 18, Acid Red 27, Acid Red 50, Acid Red 52, Acid Red 73, Acid Red 87, Acid Red 88, Acid Red 92, Acid Red 155, Acid Red 180, Acid Violet 9, Acid Violet 43, Acid Violet 49, Acid Yellow 1, Acid Yellow 23, Acid Yellow 3, Food Yellow No. 8, D&C Brown No. 1, D&C Green No. 5, D&C Green No. 8, D&C Orange No. 4, D&C Orange No. 10, D&C Orange No. 11, D&C Red No. 21, D&C Red No. 27, D&C Red No. 33, D&C Violet 2, D&C Yellow No. 7, D&C Yellow No. 8, D&C Yellow No. 10, FD&C Red 2, FD&C Red 40, FD&C Red No. 4, FD&C Yellow No. 6, FD&C Blue 1, Food Black 1, Food Black 2, Disperse Black 9, Disperse Violet 1, HC Blue 18, HC Red 18 and HC Yellow 16 and their alkali metal salts such as sodium, potassium. Among those, the most preferred anionic dyestuffs are Acid Red 52, DC Violet 2, DC Red 33, DC Orange 4, DC Red 27, DC Yellow 10, HC Blue 18, HC Red 18 and HC Yellow 16.

Suitable cationic dyes are in principle those available on the market for cosmetic hair colouring applications. For this purpose, special reference is made to the PCT application WO 95/15144 of Ciba-Geigy AG. Some examples to those are Basic Blue 6, Basic Blue 7, Basic Blue 9, Basic Blue 26, Basic Blue 41, Basic Blue 99, Basic Brown 4, Basic Brown 16, Basic Brown 17, Natural Brown 7, Basic Green 1, Basic Red 2, Basic Red 12 Basic Red 22, Basic Red 76, Basic Violet 1, Basic Violet 2, Basic Violet 3, Basic Violet 10, Basic Violet 14, Basic Yellow 57, Basic red 51, Basic Yellow 87 Basic Orange 31 and HC Blue 17. The most preferred ones are Basic red 51, Basic Yellow 87 and Basic Orange 31 sold by BASF, and HC Blue 17.

Suitable nitro dyes are HC Blue No. 2, HC Blue No. 4, HC Blue No. 5, HC Blue No. 6, HC Blue No. 7, HC Blue No. 8, HC Blue No. 9, HC Blue No. 10, HC Blue No. 11, HC Blue No. 12, HC Blue No. 13, HC Brown No. 1, HC Brown No. 2, HC Green No. 1, HC Orange No. 1, HC Orange No. 2, HC Orange No. 3, HC Orange No. 5, HC Red BN, HC Red No. 1, HC Red No. 3, HC Red No. 7, HC Red No. 8, HC Red No. 9, HC Red No. 10, HC Red No. 11, HC Red No. 13, HC Red No. 54, HC Red No. 14, HC Violet BS, HC Violet No. 1, HC Violet No. 2, HC Yellow No. 2, HC Yellow No. 4, HC Yellow No. 5, HC Yellow No. 6, HC Yellow No. 7, HC Yellow No. 8, HC Yellow No. 9, HC Yellow No. 10, HC Yellow No. 11, HC Yellow No. 12, HC Yellow No. 13, HC Yellow No. 14, HC Yellow No. 15, 2-Amino-6-chloro-4-nitrophenol, picramic acid, 1,2-Diamino-4-nitrobenzol, 1,4-Diamino-2-nitrobenzol, 3-Nitro-4-aminophenol, 1-Hydroxy-2-amino-3-nitrobenzol and 2-hydroxyethylpicramic acid.

Plant dyestuffs can also be used alone or in combination with synthetic direct-acting dyestuffs, for example henna (red or black), alkanna root, laccaic acid, indigo, logwood powder, madder root and rhubarb powder, etc.

The composition B comprises one or more hair direct dye at a total concentration of 0.01% to 10%, preferably 0.05% to 7.5% and more preferably 0.1% to 5% by weight calculated to the total of the composition B. The composition can also comprise mixtures of several direct dyes, i.e., anionic, cationic and/or nonionic ones. In such a case the dyes may be mixed at any ratio with each other.

The composition B comprises furthermore one or more alkalizing agents. The suitable ones are same as the ones disclosed above for the composition A and preferred are ammonia, monoethanolamine, and aminomethylpropanol, and particularly suitable one is aminomethylpropanol.

The alkalizing agent is comprised in the composition B at a total concentration of 1% to 20%, preferably 1% to 17.5%, more preferably 2% to 15% and most preferably 2.5% to 13% by weight calculated to the total of the composition B.

The pH of the composition B is in the range of 7.1 to 12, preferably 9 to 11, more preferably 9 to 10.5 and most preferably 9.5 to 10.5.

The composition C is an aqueous composition and comprises one or more oxidizing agent(s). The oxidizing agents suitable are hydrogen peroxide, urea peroxide, melamin peroxide or perborate salts. The most preferred is hydrogen peroxide. The composition C comprises one or more oxidizing agents at a total concentration of 0.75% to 20% by weight, preferably 1% to 15%, more preferably 2% to 12% and most preferably 3% to 12% by weight, calculated to the total of composition C. The composition C may be in the form of a solution, thickened gel or an emulsion. Emulsion form is particularly preferred.

The composition D comprises
i—one or more carboxylic acids having three or more carboxyl groups and/or their salts, and
ii—one or more additional organic acid and/or their salts having one or two carboxyl groups.

Suitable carboxylic acids with three or more carboxyl groups and/or their salts are citric acid, ethylenediamine tetraacetic acid (EDTA), pyromellitic acid and glutamate diacetate. The ethylenediamine tetraacetic acid (EDTA) and/or its salts such as monosodium, disodium, trisodium and tetrasodium salts are the most preferred ones.

Suitable organic acids with one or two carboxyl groups and/or their salts are acetic acid, malic acid, lactic acid, glycolic acid, tartaric acid, formic acid, oxalic acid, malonic acid, succinic acid, glutaric acid, adipic acid, maleic acid, and fumaric acid. In the preferred embodiment of the present invention the composition D comprises, as the second acid, one or more organic acids having one or two carboxyl groups and the most preferred acid is malic acid and/or its salts such as sodium, potassium and ammonium salts.

The composition D comprises the two acids at a total concentration in the range of 10% to 100% by weight, preferably 12.5% to 90%, more preferably 12.5% to 75% by weight and most preferably 12.5% to 60% by weight, calculated to the total of composition D.

The two acids are comprised in the composition D at a weight ratio of first acid (i) to second acid (ii) in the range from 10:1 to 1:250, preferably from 5:1 to 1:150, and more preferably from 2:1 to 1:100 and most preferably 1:50.

The composition D may be in the form of a powder, a dispersion, an emulsion or a solution. In a preferred embodiment of the present invention the composition D is an aqueous composition and preferably has a pH in the range of 1 to 5, preferably 2 to 4, more preferably in the range of 2.5 to 3.6. In the case that the pH must be adjusted to a certain value, the composition D comprises one or more alkalizing agents as disclosed above for the composition A. The preferred are ammonia, monoethanolamine, and aminomethylpropanol and the aminomethylpropanol is particularly preferred.

The alkalizing agent is comprised in the composition D at a total concentration of 1% to 20%, preferably 1% to 17.5%, more preferably 2% to 15% and most preferably 2.5% to 13% by weight calculated to the total of the composition D.

In a further preferred embodiment of the present invention, the composition D comprises one or more thickening polymers selected from anionic, nonionic, cationic and amphoteric polymers, preferably selected from polymers with a viscosity of at least 500 mPa·s measured at a polymer concentration of 1% by weight in water and at 20° C. with a Brookfield viscometer, such as at 10 rpm for 1 minute, with an appropriate spindle.

Suitable polymers are cellulose polymers, alginates, polysaccharides and acrylic acid polymers, preferably methyl cellulose, ethyl cellulose, hydroxyethylcellulose, methylhydroxyethylcellulose, methylhydroxypropylcellulose, carboxymethyl cellulose, alginic acids, sodium alginates, ammonium alginates, calcium alginates, gum arabic, guar gum or xanthan gum, dehydroxanthan gum or acrylic acid polymers known with the CTFA adopted name Carbomer and its derivatives.

The preferred polymers are dehydroxanthan gum, xanthan gum, and polymeric anionic thickeners Carbomer and its derivatives. The particularly preferred thickening agent is dehydroxanthan gum. The thickening agents are preferably comprised in the composition D at a total concentration in the range of 0.1% to 5%, preferably, 0.2% to 3%, more preferably 0.25% to 2.5% and most preferably 0.3% to 2% by weight calculated to the total of the composition D.

The direct dyes disclosed above may also be comprised in the composition D at the same concentration ranges as disclosed above for the composition B.

The pH of the ready to use composition obtained by mixing the compositions A and D which is applied in step c of the process of present invention, is in the range of 6.5 to 11, preferably 7.5 to 10.5, more preferably 7.8 to 10 measured at 20° C.

The pH of the ready to use composition applied in step g which is obtained by mixing the compositions B, C and D is in the range of 6.5 to 11, preferably 6.8 to 10.5.

Any of the compositions A, B, C and/or D may comprise one or more of the commonly used hair conditioning compounds. These compounds are for example fatty alcohols, surfactants such as anionic, nonionic, cationic and amphoteric ones, ubiquinones, ceramides, organic solvents, lipophilic ingredients such as vegetable oils, mineral oils, silicones, fatty acid fatty alcohol esters, preservatives, amino acids, and polyols. It should be noted that these compounds are optionally comprised in the any of the compositions and their incompatibility must be carefully considered prior to addition in the compositions.

Any of the composition may comprise one or more fatty alcohols. In particular the compositions A and/or B may be aqueous compositions and may further be in the form of an emulsion and then comprise preferably one or more fatty alcohols. Suitable fatty alcohols are the ones with the chain length of 14 to 22 C atoms which may be saturated or unsaturated, linear or branched which may as well be substituted. Non-limiting examples are myristyl alcohol, cetyl alcohol, stearyl alcohol, behenyl alcohol and cetostearyl alcohol.

The total concentration of fatty alcohol is in the range from 0.1% to 20%, preferably 0.5% to 15%, more preferably 1% to 10% by weight, calculated to the total of each composition.

Compositions A, B, C, and/or D according to the present invention may comprise surfactants selected from anionic, nonionic, amphoteric and/or cationic surfactants. The anionic, nonionic, amphoteric surfactants are used generally as emulsifier or solubilizer whereas the cationic surfactants are at the same time particularly used as hair conditioners.

Anionic surfactants suitable are in principle known from the cleansing compositions. These are anionic surfactants of the sulfate, sulfonate, carboxylate and alkyl phosphate type, for example, the known $C_{10}$-$C_{18}$-alkyl sulfates, and in particular the respective ether sulfates, for example, $C_{12}$-$C_{14}$-alkyl ether sulfate, lauryl ether sulfate, especially with 1 to 4 ethylene oxide groups in the molecule, monoglyceride (ether) sulfates, fatty acid amide sulfates obtained by ethoxylation and subsequent sulfatation of fatty acid alkanolamides, and the alkali salts thereof, as well as the salts of long-chain mono- and dialkyl phosphates.

Additional anionic surfactants useful within the scope of the invention are α-olefin sulfonates or the salts thereof, and in particular alkali salts of sulfosuccinic acid semiesters, for example, the disodium salt of monooctyl sulfosuccinate and alkali salts of long-chain monoalkyl ethoxysulfosuccinates.

Suitable surfactants of the carboxylate type are alkyl polyether carboxylic acids and the salts thereof as well as alkyl amido polyether carboxylic acids and salts thereof. Such products have been known for some time and are on the market, for example, under the trade name "AKYPO®" and "AKYPO-SOFT®".

Also useful are $C_8$-$C_{20}$-acyl isethionates, alone or in admixture with other anionic surfactants, as well as sulfofatty acids and the esters thereof.

Further suitable anionic surfactants are also $C_8$-$C_{22}$-acyl aminocarboxylic acids or the water-soluble salts thereof. Especially preferred is N-lauroyl glutamate, in particular as sodium salt, as well as, for example, N-lauroyl sarcosinate, N—$C_{12}$-$C_{18}$-acyl asparaginic acid, N-myristoyl sarcosinate, N-oleoyl sarcosinate, N-lauroyl methylalanine, N-lauroyl lysine and N-lauroyl aminopropyl glycine, preferably in form of the water-soluble alkali or ammonium, in particular the sodium salts thereof, preferably in admixture with the above-named anionic surfactants.

It is also possible to use mixtures of several anionic surfactants.

Further surfactants suitable are nonionic surfactants. Non-limiting examples are long-chain fatty acid mono- and dialkanolamides, such as coco fatty acid mono- or diethanolamide and myristic fatty acid mono or diethanolamide, stearic acid mono or diethanolamide, alkyl polyglucosides with an alkyl group of 8 to 18 carbon atoms, and with 1 to 5 glucoside units, sorbitan esters, such as polyethylene glycol sorbitan stearic, myristic, palmitic, lauric acid esters, fatty acid polyglycol esters or polycondensates of ethylene-oxide and propyleneoxide, as they are on the market, for example, under the trade name "Pluronics®", as well as fatty alcohol ethoxylates, $C_{10}$-$C_{22}$-fatty alcohol ethoxylates, known by the generic terms "Laureth", "Myristeth", "Oleth", "Ceteth", "Deceth", "Steareth" and "Ceteareth" according to the CTFA nomenclature, including addition of the number of ethylene oxide molecules, e.g., "Laureth-16": The average degree of ethoxylation thereby ranges between about 2 and about 100, preferably about 10 and about 30.

Suitable amphoteric surfactants are in particular the various known betaines such as alkyl betaines, fatty acid amidoalkyl betaines and sulfobetaines, for example, lauryl hydroxysulfobetaine; long-chain alkyl amino acids, such as cocoaminoacetate, cocoaminopropionate and sodium coco-amphopropionate and -acetate have also proven suitable.

Suitable cationic surfactants are according to the general structure

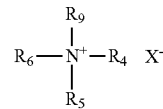

where $R_5$ is a saturated or unsaturated, branched or linear alkyl chain with 8-22 C atoms or

where $R_7$ is saturated or unsaturated, branched or linear alkyl chain with 7-21 C atoms and n has typical value of 1-4 or

where $R_8$ is saturated or unsaturated, branched or linear alkyl chain with 7-21 C atoms and n has typical value of 1-4, and $R_4$ is H or unsaturated or saturated, branched or linear alkyl chain with 1-22 C atoms or

or

where $R_7$, $R_8$ and n are same as above.

$R_9$ and $R_6$ are H or lower alkyl chain with 1 to 4 Carbon atoms, and X is typically chloride, bromide, methosulfate.

Typical examples of those ingredients are cetyl trimethyl ammonium chloride, stearyl trimonium chloride, dipalmitoyl dimonium chloride, distearyl dimethyl ammonium chloride, stearamidopropyl trimonuim chloride, dioleoylethyl dimethyl ammonium methosulfate, dioleoylethyl hydroxyethylmonium methosulfate.

Concentration of one or more total surfactants in any of the compositions A, B, C and/or D is in the range of 0.1% to 20%, preferably 0.2% to 15% and most preferably 0.2% to 10% by weight, calculated to the total of each composition.

The compositions A, B, C and/or D may further comprise lipophilic ingredients such as vegetable oils, for example, jojoba oil or any other; liquid paraffins, especially paraffinum perliquidum and parafiinum subliquidurn, silicones for example linear polysiloxanes such as dimethicones with various consistency and dimethiconols, aminated silicones with primary, secondary, tertiary or quaternary ammonium groups such as amodimethicone, polysilicone 9, and quaternium 80, cyclic silicones such as cyclomethicones, arylated silicones such as phenyl trimethicone; fatty acid esters such as octyl palmitate, isocetyl palmitate, isopropyl palmitate and octyl stearate, $C_{10}$- to $C_{36}$-fatty acid triglycerides, as well as their mixtures. Total concentration of these lipophilic compounds is in the range of 0.1% to 20% by weight, preferably from 1% to 15% by weight, and more preferably from 2% to 10% by weight, calculated to the total of each composition.

Compositions A, B, C and/or D can also comprise cationic polymers as conditioning and/or thickening agents. Those are cationic cellulose type polymers know as Polymer JR type from Amerchol such as Polyquaternium 10 or cationic guar gum known with trade name Jaguar from Rhone-Poulenc and chemically for example Guar hydroxypropyl trimonium chloride. Furthermore, chitosan and chitin can also be included in the compositions as cationic natural polymers.

Furthermore, it has been found suitable those cationic polymers known with their CTFA category name Polyquaternium. Typical examples of those Polyquaternium 4, Polyquaternium 6, Polyquaternium 7, Polyquaternium 10, Polyquaternium 11, Polyquaternium 16, Polyquaternium 22, Polyquaternium 24, Polyquaternium 28, Polyquaternium 30, Polyquaternium 37, Polyquaternium 36, Polyquaternium 46, Polyquaternium 67, and Polyquaternium 72.

Equally suitable are those polymers known with their CTFA category name Quaternium are suitable. Those are for example Quaternium-8, Quaternium-14, Quaternium-15, Quaternium-18, Quaternium-22, Quaternium-24, Quaternium-26, Quaternium-27, Quaternium-30, Quaternium-33, Quaternium-53, Quaternium-60, Quaternium-61, Quaternium-72, Quaternium-78, Quaternium-80, Quaternium-81, Quaternium-82, Quaternium-83 and Quaternium-84.

The total concentration of cationic polymers may be in the range of 0.1% to 7.5% by weight, preferably 0.3% to 5% by weight and more preferably 0.5% to 2.5% by weight, calculated to the total of each composition Composition A, B, C and/or D may comprise one or more ceramide compound, such as the one according to general formula

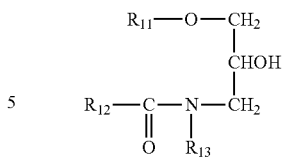

where $R_{11}$ and $R_{12}$ are independent from each other an alkyl- or alkenyl group with 10 to 22 carbon atoms, $R_{13}$ is alkyl or hydroxyl alkyl with 1 to 4 carbon atoms group and n is a number between 1 to 6, preferably 2 or 3. Preferred compound according to the above chemical structure is cetyl-PG-hydroxyethylpalmitamide. Concentration of ceramide type of compounds ranges from 0.01% to 2%, preferably 0.01% to 1% by weight calculated to the total of each composition.

The compositions A and/or B may comprise ubiquinone of the formula:

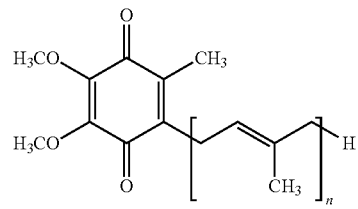

wherein n is a number from 1 to 10. Concentration of ubiquinone can vary between 0.001% and 10% by weight, calculated to the total of each composition.

The compositions A, B, C and/or D may comprise one or more organic solvent such as 2-phenoxyethanol, benzyl alcohol, 2-phenylethanol and 2-benzyloxyethanol. Suitable aliphatic alcohols are ethanol, isopropanol, propanol, n-butanol, isobutanol, t-butanol and 1-pentanol. Concentration of one or more organic solvent is in the range of 0.1% to 15%, preferably 0.5% to 12.5% and more preferably 1% to 10% and most preferably 1% to 7.5% by weight calculated to the total of each composition.

The compositions A, B, C and/or D may further comprise one or more amino acids, preferably at a concentration in the range of 0.01% to 5%, preferably 0.1% to 3% and more preferably 0.2% to 2.5% and most preferably 0.25% to 2% by weight calculated to the total of each composition. Suitable ones are all of the known amino acids such as, arginine, alanine, asparagine, glutamine, glycine, histidine, leucine, lysine, methionine, phenylalanine, proline, serine, threonine, tryptophan, tyrosine and valine.

The compositions A, B, C and/or D may further comprise one or more polyol, preferably at a concentration in the range of 0.01% to 5%, preferably 0.1% to 3% and more preferably 0.2% to 2.5% and most preferably 0.25% to 2% by weight calculate to the total of each composition. Suitable ones are propylene glycol, diproplylene glycol, glycerine, panthenol and its derivatives.

The compositions A, B, C and/or D may further comprise any known preservatives if necessary.

After rinsing off the reducing composition in step c and prior to application of the composition C and or prior to releasing the tension from hair, an aqueous intermediate treatment composition may preferably be used in order to de-swell hair for minimizing further damage to the hair fibre. The intermediate composition is applied onto hair after rinsing off the reducing composition but before applying the oxidizing composition and preferably left on the hair up to 15 min, more preferably up to 10 min and optionally rinsed off from hair prior to application of the oxidizing composition in steps d or e. The intermediate composition comprises one or more inorganic salt, preferably at a concentration of 0.5% to 15%, more preferably 1% to 12.5% and most preferably 2% to 12.5% by weight calculated to the total of the composition.

In principle any water soluble inorganic salt is suitable for the purpose. In the preferred embodiment, salts are preferably selected from salts of mono or divalent cations with mono and divalent anions. Preferred cations are sodium, calcium, potassium and magnesium and anions are chloride and sulfate. Suitable ones are such as sodium chloride, sodium sulfate, magnesium sulfate, potassium chloride, potassium sulfate, magnesium chloride, calcium chloride, ammonium salts such as ammonium chloride and ammonium sulfate. Additionally salts have been found to be especially suitable such as iodide ions especially potassium and sodium salts, copper chloride, copper sulphate, cobalt chloride, cerium sulphate, cerium chloride, vanadium sulphate, lithium chloride, magnesium acetate, calcium nitrate, barium nitrate, magnesium oxide, and ammonium nitrate. Preferred inorganic salts are sodium chloride, sodium sulfate, magnesium sulfate, potassium chloride, potassium sulfate, magnesium chloride, calcium chloride and salts of iodide ions. More preferably the salts are sodium chloride, sodium sulfate, magnesium sulfate, potassium chloride, potassium sulfate, magnesium chloride and salts of iodide ions especially potassium and sodium salts. In particular, with magnesium sulfate, sodium chloride and potassium iodide exceptionally good results are observed.

The intermediate treatment composition may preferably comprise an oxidizing agent at a concentration of 0.1% to 5%, preferably 0.2% to 5% more preferably 0.2% to 3% and most preferably 0.2% to 2% by weight calculated to the total of the composition. Suitable oxidizing agents are hydrogen peroxide and sodium bromate. Most preferred is hydrogen peroxide.

The intermediate treatment composition has a pH between 2 and 7, preferably 2.5 and 6 and more preferably 3 and 5.

The following examples are to illustrate the invention, but not to limit it.

EXAMPLE 1

The Composition A

|  | % by weight |
| --- | --- |
| Ammonium thioglycolate (60%) | 21.3 |
| Ammonium hydrogen carbonate | 5.0 |
| 1,3-butylene glycol | 3.0 |
| Amodimethicone | 0.2 |
| PEG-40-Hydrogenated castor oil | 0.7 |
| Fragrance | 0.4 |
| Ammonia, 25% | ad pH 8.3 |
| Water | ad 100.0 |

The Composition B

|  | % by weight |
| --- | --- |
| Cetearyl alcohol | 10.0 |
| Cocamide MEA | 4.0 |
| Sodium lauryl sulphate | 1.5 |
| Propylene glycol | 2.0 |
| Cetyltrimonium chloride | 0.5 |
| 2,5,6-Triamino-4-hydroxypyrimidine sulphate | 0.01 |
| 2,5-Diaminotoluene sulphate | 0.55 |
| 4-Chlororesorcinol | 0.17 |
| Resorcinol | 0.05 |
| 3-Aminophenol | 0.03 |
| Sodium sulfite | 1.0 |
| Aminomethylpropanol | 2.0 |
| Ammonium hydroxide | q.s. to pH 10.0 |
| Fragrance, preservative | q.s. |
| Water | to 100 |

The Composition C

|  | % by weight |
| --- | --- |
| Hydrogen peroxide | 2 |
| Phosphoric acid | q.s. to pH 3.5 |
| Water | to 100 |

The Composition D

|  | % by weight |
| --- | --- |
| Tetrasodium EDTA | 1.0 |
| Malic acid | 13.0 |
| Aminomethylpropanol | 6.0 |
| Hydroxypropyl xanthan gum | 0.6 |
| Cetrimonium chloride | 0.1 |
| Preservative | q.s. |
| Water | to 100 |

The pH of the above composition D is approximately 3.5.

Caucasian hair of 25 cm length was obtained from Fischbach+Miller, Laupheim, Germany. The hair streaks were permanently straightened and dyed with the above compositions. First, the hair was shampooed with a Dualsenses Deep Cleansing Shampoo, towel dried and put on curlers and the reducing composition (the composition A) given above was applied onto hair after mixing with the composition D at a weight ratio of composition A to D 10:0.2 and processed for about 15 minutes. Then the composition was rinsed off from the hair and the dyeing composition obtained by mixing the compositions B, C and D at a weight ratio of 1:2:0.2 was applied onto hair. The resulting composition had a pH of approximately 9.5. The composition was applied onto streaks of human hair and left on the hair for 30 min at ambient temperature, then rinsed off from the hair and the hair was shampooed with a Dualsenses Color Protection Shampoo and dried (inventive process).

For comparison purposes a similar process of above was applied to hair with the exception that composition D was replaced with an equal amount of water instead of composition D (comparative process).

Evenness of perm and color durability were investigated on pre-damaged hair. Damage was conferred to hair by bleaching hair with a commercially available bleaching composition under the brand Goldwell. Then, the inventive and comparative process of above was applied to hair. The result was recorded by measuring spreading of the hair streaks and calculation of a volume factor based on the spreading of hair at the root and at the tip parts. In other words, width of hair streaks were measured at their root and at their tips by placing the hair streaks on millimeter paper. A volume factor was calculated according to equation (1):

$$Volume factor = \frac{\text{Width at hair tips [cm]}}{\text{Width at hair root [cm]}} \quad \text{Equation (1)}$$

Hair streaks before treatment displayed a volume factor of 1.2. As a result of the experiments, the hair treated with the inventive process had a volume factor of 1.45, whereas the hair treated with the comparative process had a volume factor of 2.63. In conclusion, the comparative process led to a much higher increase of hair volume which is definitively undesired by the customer as a result of a straightening process. The inventive process did not lead to such an increase.

Color durability was investigated by incubating the hair streaks in a shaking bath with a shaking frequency of 100 min$^{-1}$ for 15 min at 30° C. The water bath was filled with an aqueous solution of sodium laureth sulfate at a concentration of 5% by weight, calculated to the total of the water bath solution. Upon incubation, the hair streaks were rinsed with water and towel dried. Color results were measured prior to incubation and upon incubation by spectrophotometrical analysis with a Datacolor 45G CT instrument delivered from Datacolor Inc., Lawrenceville, N.J., USA. Based on the CIE*Lab color space results obtained by the measurements, $\Delta E_{ab}$ values for color difference were calculated according to equation (1):

$$\Delta E_{ab} = \sqrt{(L_2-L_1)+(a_2-a_1)+(b_2-b_1)} \quad \text{Equation 1}$$

The $\Delta E_{ab}$ value for hair streaks treated with the inventive process was 10.93, whereas the $\Delta E_{ab}$ value for the hair streaks treated with the comparative process was 13.75. Lower $\Delta E_{ab}$ values correspond to less change in hair color upon incubation and the results clearly showed that the inventive process led to a much lower color change which differs to the comparative process by approximately 3 color units. In conclusion the presented data clearly showed the superior performance of the inventive process compared to the state-of-the-art process.

EXAMPLE 2

Intermediate Composition

|  | % by weight |
| --- | --- |
| Magnesium sulfate | 10 |
| Cetrimonium chloride | 0.5 |
| Citric acid | q.s. to pH 4.2 |
| Water | q.s. to 100 |

In the process disclosed with Example 1 above, the intermediate treatment composition was applied onto hair after rinsing off the reducing composition. The intermediate treatment composition was left on hair for 5 min and without rinsing it off the composition of step e was applied. The permanent shaping and dyeing results observed with the Example 1 were confirmed.

Similar results were obtained with the following compositions.

EXAMPLE 3

The Composition D

|  | % by weight |
| --- | --- |
| Tetrasodium EDTA | 5.0 |
| Malic acid | 15.0 |
| Aminomethylpropanol | 6.0 |
| Hydroxypropyl xanthan gum | 0.6 |
| Cetrimonium chloride | 0.1 |
| Preservative | q.s. |
| Water | to 100 |

The pH of the above composition D was approximately 3.6.

EXAMPLE 4

The Composition D

| Component | % by weight |
| --- | --- |
| AMP | 6.0 |
| Tetrasodium EDTA | 3.0 |
| Malic acid | 13.0 |
| Lactic acid | 4.0 |
| Hydroxypropyl xanthan gum | 0.6 |
| Polyquaternium-10 | 0.1 |
| Water | to 100 |
| pH | 3.4 ± 0.1 |

EXAMPLE 5

The Composition D

| Component | % by weight |
| --- | --- |
| Monoethanolamine (MEA) | 2.7 |
| Tetrasodium EDTA | 5.0 |
| Malic acid | 15.0 |
| Hydroxypropyl xanthan gum | 0.6 |
| Panthenol | 0.1 |
| Water | To 100 |
| pH | 3.3 ± 0.1 |

EXAMPLE 6

The Composition D

| Component | % by weight |
| --- | --- |
| AMP | 6.0 |
| Citric acid | 5.0 |
| Maleic acid | 15.0 |
| Hydroxypropyl xanthan gum | 0.6 |
| Behenamidopropyl trimonium chloride | 0.2 |
| Water | to 100 |
| pH | 1.5 ± 0.1 |

EXAMPLE 7

The Composition D

| Component | % by weight |
|---|---|
| MEA | 2.0 |
| Lactic acid | 15.0 |
| Citric acid | 6.0 |
| Hydroxypropyl xanthan gum | 0.6 |
| Polyquaternium-67 | 0.1 |
| Water | to 100 |
| pH | 2.7 ± 0.1 |

EXAMPLE 8

The Composition D

| | % by weight |
|---|---|
| Tetrasodium EDTA | 1.0 |
| Malic acid | 13.0 |
| Aminomethylpropanol | 6.0 |
| Basic red 51 | 1.00 |
| HC red XX | 1.00 |
| Hydroxypropyl xanthan gum | 0.6 |
| Cetrimonium chloride | 0.1 |
| Preservative | q.s. |
| Water | to 100 |

The pH of the composition was 3.5.

EXAMPLE 9

The Composition A

| | % by weight |
|---|---|
| Ammonium thioglycolate (60%) | 0.9 |
| Cystein hydrochloride | 5.7 |
| Ammonium hydrogen carbonate | 1.5 |
| Acetylcystein | 0.7 |
| Cetrimonium chloride | 0.1 |
| 1,3-butylene gylcol | 0.5 |
| Amodimethicone | 0.2 |
| Fragrance | 0.4 |
| Ammonia, 25% | ad pH 9.8 |
| Water | q.s. 100.0 |

The composition B and C were same as Example 1.

The Composition D

| | % by weight |
|---|---|
| Tetrasodium EDTA | 4.0 |
| Malic acid | 17.0 |
| Aminomethylpropanol | 6.0 |
| Hydroxypropyl xanthan gum | 0.6 |
| Cetrimonium chloride | 0.1 |
| Preservative | q.s. |
| Water | to 100 |

The pH of the composition was 3.4.

EXAMPLE 10

The Composition D (Powder)

| | % by weight |
|---|---|
| Tetrasodium EDTA | 7.0 |
| Malic acid | 92.0 |
| Hydroxyethylcellulose | 1.0 |

1 g of the composition above was added to the mixture of 30 g of composition A of example 1. After mixing thoroughly, the resulting composition was applied onto hair which was already put under tension using curlers and rinsed off after leaving it on the hair for 30 min. The hair was released from tension and the dyeing composition obtained by mixing the compositions B (20 g), C (20 g) and D (1 g) was applied onto hair and after leaving on the hair for 30 min rinsed off from hair and hair was shampooed and dried. It was observed that the hair was effectively and homogeneously curled and dyed and had its natural softness and elasticity.

EXAMPLE 11

The Composition D

| | % by weight |
|---|---|
| EDTA monosodium salt | 1.0 |
| Malic acid | 13.0 |
| Aminomethylpropanol | 6.0 |
| Hydroxypropyl xanthan gum | 0.6 |
| Cetrimonium chloride | 0.1 |
| Preservative | q.s. |
| Water | to 100 |

The pH of the above composition D is approximately 3.1.

EXAMPLE 12

The Composition D

| | % by weight |
|---|---|
| EDTA disodium salt | 1.0 |
| Malic acid | 13.0 |
| Aminomethylpropanol | 6.0 |
| Hydroxypropyl xanthan gum | 0.6 |
| Cetrimonium chloride | 0.1 |
| Preservative | q.s. |
| Water | to 100 |

The pH of the above composition D is approximately 3.2.

EXAMPLE 13

The Composition D

| | % by weight |
|---|---|
| EDTA trisodium salt | 1.0 |
| Malic acid | 13.0 |
| Aminomethylpropanol | 6.0 |
| Hydroxypropyl xanthan gum | 0.6 |
| Cetrimonium chloride | 0.1 |

-continued

| | % by weight |
|---|---|
| Preservative | q.s. |
| Water | to 100 |

The pH of the above composition D is approximately 3.4.

The invention claimed is:

1. A process for treating hair, the process comprising:
a) washing hair with a cleansing composition and towel drying the washed hair to provide dried hair;
b) applying a first ready to use composition onto the dried hair and leaving the first ready to use composition on the dried hair for a first time period ranging from 1 minute to 30 minutes, wherein the first ready to use comprises a composition A that is an aqueous composition comprising one or more reducing agents and one or more alkalizing agents and having a pH value ranging from 7.5 to 12.0;
c) rinsing the first ready to use composition off the dried hair with water to provide a rinsed hair;
d) optionally applying a composition C onto the rinsed hair, wherein the composition C is an aqueous composition comprising one or more oxidizing agents and having a pH value ranging from 1.5 to 5;
e) applying a second ready to use composition onto the rinsed hair, and leaving the second ready to use composition on the rinsed hair for a second time period ranging from 1 minute to 45 minutes to provide a dyed hair, wherein the second ready to use composition comprises the composition C and a composition B that is an aqueous composition comprising one or more hair dyes and one or more alkalizing agents and having a pH value ranging from 7.1 to 12; and
f) rinsing the second ready to use composition off the dyed hair,
wherein
the first ready to use composition has a pH value in the range of 6.5-11 and is obtained by mixing the composition A with a composition D immediately before application onto the hair,
the second ready to use composition has a pH value ranging from 6.5 to 11 and is obtained by mixing the composition B and the composition C with the composition D immediately before application onto the hair,
the composition D has a pH value ranging from 1 to 5 and comprises:
i) one or more carboxylic acids having three or more carboxyl groups and/or their salts, and
ii) one or more additional organic acids and/or their salts having two carboxyl groups,
the composition D comprises the acids of i) and ii) and/or their salts at a total concentration of 10% to 100% by weight, calculated to a total weight of the composition D, and
each of the first and second ready to use compositions comprises the acids of i) and ii) and/or their salts at a total concentration ranging from 1% to 10% by weight, calculated to a total weight of each of the first and second ready to use compositions.

2. The process of claim 1,
wherein
the one or more carboxylic acids with three or more carboxyl groups is selected from the group consisting of citric acid, ethylenediamine tetraacetic acid (EDTA), pyromellitic acid, and glutamate diacetate,
the one or more additional organic acids with two carboxyl groups is selected from the group consisting of acetic acid, malic acid, lactic acid, glycolic acid, tartaric acid, formic acid, oxalic acid, malonic acid, succinic acid, glutaric acid, adipic acid, maleic acid, and fumaric acid, and
the composition D comprises the one or more carboxylic acids of (i) and the one or more additional organic acids of (ii) at a weight ratio (i)/(ii) ranging from 10:1 to 1:250.

3. The process of claim 1, wherein the composition D is a powder, a dispersion, an emulsion, or a solution.

4. The process of claim 1,
wherein
the pH value of the composition D ranges from 2 to 4, and
the composition D further comprises one or more alkalizing agent.

5. The process of claim 1, wherein the one or more carboxylic acids with three or more carboxyl groups is EDTA and/or its salts.

6. The process of claim 1, wherein the one or more organic acids with two carboxyl groups is malic acid and/or its salts.

7. The process of claim 1, wherein the composition B further comprises one or more oxidative dye precursors, selected from the group consisting of p-phenylendiamines, p-aminophenols, and heterocyclic diamines, and optionally one or more coupling substances, selected from the group consisting of resorcinols, m-aminophenols, m-phenylendiamines, pyridines and its derivatives, and naphthols.

8. The process of claim 1, wherein at least one of the composition B and the composition D further comprises one or more hair direct dye selected from the group consisting of cationic dyes, anionic dyes, nitro dyes, and mixtures thereof.

9. The process of claim 1, wherein the composition D further comprises at least one alkalizing agent, and at least one of the composition A, the composition B, and the composition D comprises at least one alkalizing agent selected from ammonia, alkyl- or alkanolamines according to the general structure

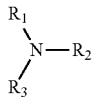

wherein $R_1$, $R_2$, and $R_3$ are the same or different, and selected from H, C1 to C4, C3 to C4 unsaturated alkyl, C3 to C4 branched alkyl, C1 to C4 hydroxyl alkyl, C3 to C4 unsaturated hydroxyl alkyl, C3 to C4 branched hydroxyl alkyl, with the condition that at least one of $R_1$, $R_2$, or $R_3$ is different from H.

10. The process of claim 1, wherein at least one of the composition A, the composition B, the composition C, and the composition D further comprises one or more ingredients selected from the group consisting of fatty alcohols, surfactants, ubiquinones, ceramides, reducing agents, organic solvents, silicones, antioxidants, preservatives, amino acids, and polyols.

11. The process of claim 1,
wherein
the composition B further comprises one or more reducing agents and the one or more reducing agents of the composition A and the composition B are selected from the group consisting of thioglycolic acid, cysteamine and/or its salts, thioglycerin and/or its salts, glycerin esters of thioglycolic acid and/or its salts, thiolactic acid and/or its salts, and cysteine or its derivatives and/or its salts,
the composition A comprises the one or more reducing agents at a concentration ranging from 1% to 15% by weight, calculated to the total weight of composition A, and/or
the composition B comprises the one or more reducing agents at a concentration ranging from 0.1% to 1.0% by weight, calculated to the total weight of composition B.

12. The process of claim 2, wherein the composition D further comprises one or more thickening polymers selected from anionic polymers, nonionic polymers, cationic polymers, and amphoteric polymers, having a viscosity of at least 500 mPa·s measured at a polymer concentration of 1% by weight in water and at 20° C. with a Brookfield viscometer, with an appropriate spindle.

13. The process of claim 12,
wherein
the one or more thickening polymers is selected from the group consisting of hydroxypropyl xanthan gum, dehydroxanthan gum, xanthan gum, and polymeric anionic thickeners,
the one or more thickening polymers are present in the composition D at a total concentration ranging from 0.1% to 5% by weight, calculated to a total weight of the composition D, and
the weight ratio (i)/(ii) ranges from 2:1 to 1:100.

14. The process of claim 4, wherein the one or more alkalizing agent is present in at least one of the composition A, the composition B, and the composition D at a concentration in the range of 0.1% to 20% by weight, calculated to a total weight of the composition A, the composition B, and the composition D, respectively.

15. The process of claim 1, further comprising:
applying the composition C onto the rinsed hair in d) prior to application of the second ready to use composition in e).

16. The process of claim 1, further comprising:
putting the dried hair under tension before or during or after application of the first ready to use composition in b); and
releasing the tension from rinsed hair before application of the second ready to use composition in e).

17. The process of claim 1, wherein the one or more oxidizing agents of the composition C is selected from the group consisting of hydrogen peroxide, urea peroxide, melamin peroxide or perborate salts.

18. The process of claim 9, wherein the one or more alkalizing agents is selected from the group consisting of ammonia, monoethanolamine, and aminomethylpropanol.

19. The process of claim 4,
wherein
the pH value of the composition D ranges from 2.5 to 3.6.

20. The process of claim 19,
wherein
the pH value of the second ready to use composition ranges from 6.8 to 10.5.

* * * * *